Bohm et al.

United States Patent [19]

[11] 4,255,417
[45] Mar. 10, 1981

[54] PLATINUM COMPOUNDS FOR THE IRRADICATION OF SKIN BLEMISHES

[75] Inventors: John D. Bohm, Cherry Hill, N.J.; James B. Hunter, Newtown Square, Pa.

[73] Assignee: Johnson Matthey, Inc., Malvern, Pa.

[21] Appl. No.: 711,640

[22] Filed: Aug. 4, 1976

[51] Int. Cl.$^3$ .................. A61K 33/24; A61K 31/28
[52] U.S. Cl. .................................. 424/131; 424/287
[58] Field of Search ........................... 424/131, 287

[56] References Cited

U.S. PATENT DOCUMENTS

| | | | |
|---|---|---|---|
| 3,892,790 | 7/1975 | Tobe et al. | 424/287 |
| 3,904,663 | 9/1975 | Tobe et al. | 424/287 |
| 4,053,587 | 10/1977 | Davidson et al. | 424/287 |

OTHER PUBLICATIONS

Connors et al., Platinum Coordination Complexes in Cancer Chemotherapy, 1974, pp. 26 and 102–104.
Andrewes, Viruses of Vertebrates, 1964, pp. 199–200.
Rosenberg et al., Nature, vol. 222, 4/26/69, pp. 385–386.
Chemical Abstracts 74:108373r, (1971).
Dillaha et al., Chemical Abstracts 66:54195x, (1967).

*Primary Examiner*—Jerome D. Goldberg
*Attorney, Agent, or Firm*—Cushman, Darby & Cushman

[57] ABSTRACT

A method of treating external skin blemishes which comprises applying to the skin an effective amount of a platinum compound having the structures:

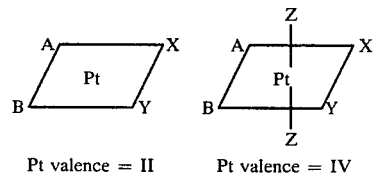

Pt valence = II     Pt valence = IV wherein X and Y are either halogens or the oxygen atoms of a carboxylate bidentete ligand and A and B comprise $NH_3$ groups or organic amines.

In the octahedral case (Pt valence=IV) Z is either halogens or hydroxyl (OH) groups.

1 Claim, No Drawings

PLATINUM COMPOUNDS FOR THE IRRADICATION OF SKIN BLEMISHES

The present invention relates to the treatment of external skin blemishes, e.g., warts and moles, on humans using a platinum compound.

Various platinum compounds have been proposed for use against tumors (see Rosenberg et al., Nature 222 (1969), pages 385–386; and U.S. Pat. Nos. 3,892,790 and 3,904,663). One such compound is cis-dichloro diamine platinum (II) which may also be called cis-platinum diamino dichloride or Cis Pt II for convenience, and may be represented by the following formula:

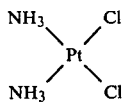

The present invention is based on the unexpected finding that Cis Pt II can be effectively used for the treatment of external skin blemishes such as warts or moles. In particular, it has been found that the application of Cis Pt II to warts and moles, or the like, eliminates these external skin blemishes. The Cis Pt II may be applied in any conventional fashion, for example, in a cream base, ointment, salve, lotion or solution (aqueous or organic solvent base).

The amount of Cis Pt II applied to the skin can be widely varied and the amount used in any specific situation, and the number of applications, will depend to some extent on the size and nature of the blemishes involved. A typical application may involve thoroughly wetting the blemishes with, for example, a saturated aqueous solution of the Cis Pt II. One such application may be adequate or the treatment may be repeated one or more times.

As a typical illustration, a saturated solution of Cis Pt II in 0.1 N aqueous sodium chloride was applied to a wart of long standing (at least several years). The application was repeated once daily for several days and then discontinued. After several more days, the wart began to gradually diminish in size, and within several weeks, had completely disappeared.

In another instance, the application of a solution of Cis Pt II (again in the form of an 0.1 N aqueous sodium chloride solution saturated with Cis Pt II), to a skin mole resulted in the complete disappearance of the mole within a short period of time.

While the invention has been specifically described above with respect to the use of Cis Pt II, it is believed that the invention is of broader application to the use of compounds related to Cis Pt II, e.g., those described and claimed in U.S. Pat. Nos. 3,892,790 and 3,904,663, and other types as detailed in Coordination Chemistry Review, 12(1974) 349–405, Dr. M. J. Cleare, "Transition Metal Complexes in Cancer Chemotherapy" (1973). Thus, in a broad sense, the invention contemplates the use of platinum compounds or coordination complexes shown by the formulas:

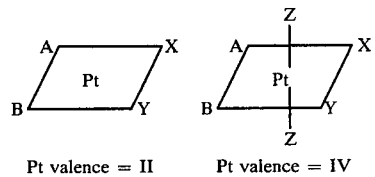

Pt valence = II    Pt valence = IV wherein X and Y are halogens, preferably chlorine or the oxygen atoms of a carboxylate bidentete ligand such as oxalate and malonate and A and B are NH$_3$ groups or organic amines such as isopropylamine, n-butylamine, cyclopentylamine, benzylamine, ethylenediamine, or, together, represent the atoms necessary to complete a phenylenediamine ring wherein the diamine groups are coordinated with the Pt atoms.

In the case of the platinum atom valance IV, A, B, X and Y represent groups as defined above, and Z represents either halogens or hydroxyl (OH) groups.

It will be appreciated that various modifications may be made in the invention as described above. Hence, the scope of the invention is defined in the following claims wherein:

We claim:

1. A method of eliminating warts and moles on the skin of a human which comprises topically applying to said wart or mole an effective amount of cis platinum diamino dichloride.

* * * * *